(12) United States Patent
Griffin et al.

(10) Patent No.: US 12,053,762 B2
(45) Date of Patent: Aug. 6, 2024

(54) ATOMICALLY DISPERSED CATALYSTS TO PROMOTE LOW TEMPERATURE BIOGAS UPGRADING

(71) Applicant: Alliance for Sustainable Energy, LLC, Golden, CO (US)

(72) Inventors: Michael Brandon Griffin, Denver, CO (US); Matthew Maurice Yung, Denver, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 17/551,968

(22) Filed: Dec. 15, 2021

(65) Prior Publication Data
US 2022/0184585 A1 Jun. 16, 2022

Related U.S. Application Data

(60) Provisional application No. 63/125,792, filed on Dec. 15, 2020.

(51) Int. Cl.
| | |
|---|---|
| B01J 21/06 | (2006.01) |
| B01J 23/10 | (2006.01) |
| B01J 23/28 | (2006.01) |
| B01J 23/42 | (2006.01) |
| B01J 23/46 | (2006.01) |
| B01J 23/63 | (2006.01) |

(Continued)

(52) U.S. Cl.
CPC .......... *B01J 23/755* (2013.01); *B01J 21/063* (2013.01); *B01J 23/10* (2013.01); *C07C 1/12* (2013.01); *C07C 2521/06* (2013.01); *C07C 2523/10* (2013.01); *C07C 2523/755* (2013.01)

(58) Field of Classification Search
CPC . B01J 21/063; B01J 23/10; B01J 23/28; B01J 23/42; B01J 23/46; B01J 23/462; B01J 23/464; B01J 23/63; B01J 23/755; B01J 23/83; B01J 23/894; B01J 23/8993
USPC ............................. 502/304, 350, 337, 339
See application file for complete search history.

(56) References Cited

U.S. PATENT DOCUMENTS

| | | | | |
|---|---|---|---|---|
| 4,847,231 A | * | 7/1989 | Gratzel | .................... B01J 23/56 502/328 |
| 5,851,950 A | * | 12/1998 | Rossin | .................. B01D 53/54 423/236 |

(Continued)

OTHER PUBLICATIONS

"HVAC Energy Breakdown", available at https://www.environment.gov.au/system/files/energy/files/hvac-factsheet-energy-breakdown.pdf., Sep. 2013, accessed on Jan. 20, 2019, pp. 1-2.

(Continued)

*Primary Examiner* — Cam N. Nguyen
(74) *Attorney, Agent, or Firm* — Neal S. Vickery

(57) ABSTRACT

Described herein are catalysts and methods for converting waste biogas (e.g., a mixture of carbon dioxide and methane) into useful products. In some embodiments, the biogas is converted into a highly purified methane, that can be further processed to generate fuel products, including recycled natural gas (RNG) and liquid fuels. The described catalysts and methods may be advantageous over conventional methods, including by reducing catalyst costs, decreasing temperature requirements and/or providing higher purity products by reducing carbon dioxide and carbon monoxide in product streams.

7 Claims, 5 Drawing Sheets

(51) Int. Cl.
*B01J 23/755* (2006.01)
*B01J 23/83* (2006.01)
*B01J 23/89* (2006.01)
*C07C 1/12* (2006.01)

(56) References Cited

U.S. PATENT DOCUMENTS

| | | | | |
|---|---|---|---|---|
| 6,168,775 | B1 * | 1/2001 | Zhou | C01B 15/029 502/344 |
| 6,326,329 | B1 * | 12/2001 | Nunan | B01J 23/10 502/263 |
| 6,335,305 | B1 * | 1/2002 | Suzuki | B01D 53/945 502/328 |
| 6,440,378 | B1 * | 8/2002 | Hirata | B01J 35/0013 502/514 |
| 6,680,279 | B2 * | 1/2004 | Cai | B01J 35/1014 502/329 |
| 6,797,669 | B2 * | 9/2004 | Zhang | C07C 5/05 502/328 |
| 6,806,225 | B1 * | 10/2004 | Ikeda | B01D 53/945 502/328 |
| 6,919,065 | B2 * | 7/2005 | Zhou | B01J 35/0013 502/262 |
| 7,169,735 | B2 * | 1/2007 | Sagae | B01J 37/0205 502/262 |
| 7,354,881 | B2 * | 4/2008 | Resasco | B82Y 15/00 502/185 |
| 7,563,742 | B2 * | 7/2009 | Reyes | B01J 35/006 502/313 |
| 7,842,644 | B2 * | 11/2010 | Kai | B01D 53/8665 502/305 |
| 8,754,270 | B2 * | 6/2014 | Weiner | B01J 23/6527 568/885 |
| 8,841,227 | B2 * | 9/2014 | Sangar | B01J 29/48 502/79 |
| 8,900,536 | B2 * | 12/2014 | Augustine | B01D 53/565 423/239.1 |
| 9,108,185 | B2 * | 8/2015 | Augustine | B01J 27/19 |
| 9,498,770 | B2 * | 11/2016 | He | B01J 23/83 |
| 9,669,393 | B2 * | 6/2017 | Karim | C10G 2/334 |
| 9,694,351 | B1 * | 7/2017 | Roy | B01J 37/16 |
| 10,159,960 | B2 * | 12/2018 | Yang | B01J 37/0236 |
| 11,052,377 | B2 * | 7/2021 | Tashita | C07C 41/30 |
| 11,471,865 | B2 * | 10/2022 | Tait | B01J 37/0209 |
| 11,518,722 | B2 * | 12/2022 | Wang | B01J 23/38 |
| 2002/0147103 | A1 * | 10/2002 | Ruettinger | B01J 23/63 502/313 |
| 2005/0009694 | A1 * | 1/2005 | Watts | B01J 37/031 502/339 |
| 2011/0034330 | A1 * | 2/2011 | Czaja | B01J 35/008 502/311 |
| 2012/0027653 | A1 * | 2/2012 | Da Costa | B01J 23/002 423/210 |
| 2013/0260433 | A1 | 10/2013 | Zhang | |
| 2014/0121097 | A1 * | 5/2014 | Phillips | B01J 35/002 502/325 |
| 2016/0346763 | A1 * | 12/2016 | Wahab | B01J 35/004 |
| 2019/0374929 | A1 * | 12/2019 | Wyman | B01J 38/02 |
| 2020/0030774 | A1 * | 1/2020 | Gao | B01J 37/10 |
| 2021/0016256 | A1 * | 1/2021 | Liu | B01J 37/035 |
| 2021/0379575 | A1 * | 12/2021 | Sasmaz | B01J 23/002 |
| 2022/0324707 | A1 * | 10/2022 | Zhou | B01J 23/755 |
| 2023/0001385 | A1 * | 1/2023 | Christopher | B01J 35/643 |
| 2023/0021410 | A1 * | 1/2023 | Aslam | C07C 4/18 |

OTHER PUBLICATIONS

Abdel-Mageed et al., "Selective CO Methanation on Ru/TiO2 Catalysts: Role and Influence of Metal-Support Interactions", ACS Catalysis, 2015, vol. 5, No. 11, pp. 6753-6763.

Aslam et al., "Anaerobic membrane bioreactors for biohydrogen production: Recent developments, challenges and perspectives", Bioresource Technology, 2018, vol. 269, pp. 452-464.

Aziz et al., "CO2 methanation over heterogeneous catalysts: recent progress and future prospects", Green Chemistry, 2015, vol. 17, pp. 2647-2663.

Barzee et al., "Digestate Biofertilizers Support Similar or Higher Tomato Yields and Quality Than Mineral Fertilizer in a Subsurface Drip Fertigation System", Frontiers in Sustainable Food Systems, 2019, vol. 3, No. 58, pp. 1-13.

Bayram et al., "Preface to the Special Issue Honoring Umit Ozkan: ACS Distinguished Researcher in Petroleum Chemistry", Topics in Catalysis, 2013, vol. 56, pp. 1601-1602.

Binnig et al., "7 x 7 Reconstruction of Si(111) Resolved in Real Space)", Scanning Tunneling Microscopy, ed. H. Neddermeyer, Springer Netherlands, Dordrecht, 1993, pp. 36-39.

Brommer et al., "Ab initio theory of the Si(111)-(7×7) surface reconstruction: A challenge for massively parallel computation", Physical Review Letters, Mar. 1992, vol. 68, No. 9, pp. 1355-1358.

Cottrill et al., "Dual phase change thermal diodes for enhanced rectification ratios: theory and experiment", Advanced Energy Materials, 2018, vol. 8, No. 11, pp. 1-11.

Daza et al., "Carbon Dioxide Conversion by Reverse Water-Gas Shift Chemical Looping on Perovskite-Type Oxides", Industrial & Engineering Chemistry Research, 2014, vol. 53, No. 14, pp. 5828-5837.

Detman et al., "Methane-yielding microbial communities processing lactate-rich substrates: a piece of the anaerobic digestion puzzle", Biotechnology for Biofuels, 2018, vol. 11, No. 116, pp. 1-18.

Es et al., "Benefits and Drawbacks of Using Two-Phase Cooling Technologies in Military Platforms", National Aerospace Laboratory NLR, NLR-TP-2011-085, 2011, pp. 1-10.

Fang et al., "Heating performance investigation of a bidirectional partition fluid thermal diode", Renewable Energy, 2010, vol. 35, No. 3, pp. 679-684.

Götz et al., "Renewable Power-to-Gas: A technological and economic review", Renewable Energy, 2016, vol. 85, pp. 1371-1390.

Gao et al., "A thermodynamic analysis of methanation reactions of carbon oxides for the production of synthetic natural gas", RSC Advances, 2012, vol. 2, pp. 2358-2368.

Gao et al., "Recent advances in methanation catalysts for the production of synthetic natural gas", RSC Advances, 2015, vol. 5, No. 29, pp. 22759-22776.

Greenhalgh et al., "Chabazite supported NiMo catalysts: Activity and sulfur poisoning", Applied Catalysis A: General, 2007, vol. 327, No. 2, pp. 189-196.

Guo et al., "Direct, Nonoxidative Conversion of Methane to Ethylene, Aromatics, and Hydrogen", Science, 2014, vol. 344, No. 6184, pp. 616-619.

Hokenek et al., "Challenges and Consequences of Carbon Dioxide as an Oxidizing Agent for Hydrogen Generation from Hydrocarbons", Technology and Innovation, 2012, vol. 14, No. 2, pp. 115-130.

Huang et al., "A General Framework for the Evaluation of Direct Nonoxidative Methane Conversion Strategies", Joule, 2018, vol. 2, pp. 349-365.

Ito et al., "Sulfur tolerance of Pd/Al2O3 and Pd/TiO2 in naphthalene hydrogenation in the presence of dimethyldisulfide", Applied Catalysis A: General, 2003, vol. 249, No. 1, pp. 19-26.

Jones et al., "Heat transfer in a liquid convective diode", Journal of Solar Energy Engineering, 1986, vol. 108, No. 3, pp. 163-171.

Koizumi et al., "Development of sulfur tolerant catalysts for the synthesis of high quality transportation fuels", Catalysis Today, 2004, vol. 89, No. 4, pp. 465-478.

Liu et al., "Pretreatment of wheat straw with potassium hydroxide for increasing enzymatic and microbial degradability", Bioresource Technology, 2015, vol. 185, pp. 150-157.

Liu et al., "Improving the bioenergy production from wheat straw with alkaline pretreatment", Biosystems Engineering, 2015, vol. 140, pp. 59-66.

Maiti et al., "Oxygen vacancy formation characteristics in the bulk and across different surface terminations of La(1-x) SrxFe(1-y)CoyO(3-δ) perovskite oxides for CO2 conversion", Journal of Materials Chemistry A, 2016, vol. 4, No. 14, pp. 5137-5148.

(56) References Cited

OTHER PUBLICATIONS

Martin et al., "High-Coverage Oxygen-Induced Surface Structures on Ag(111)", The Journal of Physical Chemistry C, 2014, vol. 118, No. 28, pp. 15324-15331.

Morejudo et al., "Direct conversion of methane to aromatics in a catalytic co-ionic membrane reactor", Science, 2016, vol. 353, No. 6299, pp. 563-566.

Ochi et al., "Development of a heat-pipe thermal diode and its heat transport performance", JSME International Journal Series B Fluids and Thermal Engineering, 1996, vol. 39, No. 2, pp. 419-425.

Quarton et al., "Power-to-gas for injection into the gas grid: What can we learn from real-life projects, economic assessments and systems modelling?", Renewable and Sustainable Energy Reviews, 2018, vol. 98, pp. 302-316.

Shan et al., "Mild oxidation of methane to methanol or acetic acid on supported isolated rhodium catalysts", Nature, 2017, vol. 551, pp. 605-608.

Shao et al., "Recent progress in the phase-transition mechanism and modulation of vanadium dioxide materials", NPG Asia Materials, 2018, vol. 10, pp. 581-605.

Splittstoesser et al., "Effect of Various Inhibitors on the Growth of Lactic Acid Bacteria in a Model Grape Juice System", Journal of Food Protection, 1989, vol. 52, No. 4, pp. 240-243.

Srimuang et al., "A review of the applications of heat pipe heat exchangers for heat recovery", Renewable and Sustainable Energy Reviews, 2012, vol. 16, No. 6, pp. 4303-4315.

Susheela et al., "Heat pipe augmented passive solar system for heating of buildings", Journal of Energy Engineering, 2001, vol. 127, No. 1, pp. 18-36.

Tao et al., "Techno-economic analysis and life-cycle assessment of cellulosic isobutanol and comparison with cellulosic ethanol and n-butanol", Biofuels, Bioproducts and Biorefining, 2014, vol. 8, No. 1, pp. 30-48.

Thang et al., "Nature of Atomically Dispersed Ru on Anatase $TiO_2$: Revisiting Old Data Based on DFT Calculations", The Journal of Physical Chemistry C, 2019, vol. 123, pp. 7271-7282.

Varga et al., "Characterisation of thermal diode panels for use in the cooling season in buildings", Energy and Buildings, 2002, vol. 34, No. 3, pp. 227-235.

Yang et al., "Interplay between Subnanometer Ag and Pt Clusters and Anatase $TiO_2$ (101) Surface: Implications for Catalysis and Photocatalysis", The Journal of Physical Chemistry C, 2014, vol. 118, No. 9, pp. 4702-4714.

Yang et al., "$CO_2$ Adsorption on Anatase $TiO_2$ (101) Surfaces in the Presence of Subnanometer Ag/Pt Clusters: Implications for $CO_2$ Photoreduction", The Journal of Physical Chemistry C, 2014, vol. 118, No. 45, pp. 26236-26248.

Yang et al., "The effect of the morphology of supported subnanometer Pt clusters on the first and key step of $CO_2$ photoreduction", Physical Chemistry Chemical Physics, 2015, vol. 17, No. 38, pp. 25379-25392.

Yang et al., "Electron injection study of photoexcitation effects on supported subnanometer Pt clusters for $CO_2$ photoreduction", Physical Chemistry Chemical Physics, 2018, vol. 20, pp. 15926-15938.

Yau et al., "A review on the application of horizontal heat pipe heat exchangers in air conditioning systems in the tropics", Applied Thermal Engineering, 2010, vol. 30, Nos. 2-3, pp. 77-84.

Yung et al., "Deactivation Mechanisms of Ni-Based Tar Reforming Catalysts as Monitored by X-ray Absorption Spectroscopy", Langmuir, 2010, vol. 26, No. 21, pp. 16589-16594.

Yung et al., "Transformation of Sulfur Species during Steam/Air Regeneration on a Ni Biomass Conditioning Catalyst", ACS Catalysis, 2012, vol. 2, No. 7, pp. 1363-1367.

Zhang et al., "Evaluating the use heat pipe for dedicated ventilation of office buildings in Hong Kong", Energy Conversion and Management, 2011, vol. 52, No. 4, pp. 1983-1989.

Zhang et al., "Effects of P/Ni ratio and Ni content on performance of γ-$Al_2O_3$-supported nickel phosphides for deoxygenation of methyl laurate to hydrocarbons", Applied Surface Science, 2016, vol. 360, Part A, pp. 353-364.

Zhu et al., "Biogas production from municipal solid wastes using an integrated rotary drum and anaerobic-phased solids digester system", Bioresource Technology, 2010, vol. 101, No. 16, pp. 6374-6380.

Zhu et al., "Temperature-gated thermal rectifier for active heat flow control", Nano Letters, 2014, vol. 14, No. 8, pp. 4867-4872.

* cited by examiner

ATOMICALLY DISPERSED CATALYSTS TO PROMOTE LOW TEMPERATURE BIOGAS UPGRADING

CROSS-REFERENCE TO RELATED APPLICATIONS

This application claims priority from U.S. Provisional Patent Application No. 63/125,792, filed on Dec. 15, 2021, the contents of which are incorporated herein by reference in their entirety.

CONTRACTUAL ORIGIN

This invention was made with government support under Contract No. DE-AC36-08GO28308 awarded by the Department of Energy. The government has certain rights in the invention.

SUMMARY

Described herein are catalysts and methods for converting waste biogas (e.g., a mixture of carbon dioxide and methane) into useful products. In some embodiments, the biogas is converted into a highly purified methane, that can be further processed to generate fuel products, including recycled natural gas (RNG) and liquid fuels. The described catalysts and methods may be advantageous over conventional methods, including by reducing catalyst costs, decreasing temperature requirements and/or providing higher purity products by reducing carbon dioxide and carbon monoxide in product streams.

The described atomically dispersed catalysts have unique physical and chemical properties compared to conventional catalysts, and they can be employed to impart low temperature activity during biogas conversion reactions performed in the presence of hydrogen (either as a reactant, intermediate, or product). For example, initial experiments have demonstrated a 10× improvement in the rate of low temperature methanation on a metal loading basis compared to a conventional Ni/$Al_2O_3$ catalyst. The observed performance improvements may be related to (1) the enhanced ability of isolated metal sites to activate hydrogen and (2) the promotion hydrogen spillover, coupled with decreased diffusion distances, to maintain the desired oxidation state and preserve catalyst activity.

The described catalysts and methods address several barriers that have inhibited wide-spread commercialization of waste-gas upgrading technologies by enabling the following advantages over conventional approaches:
  Lower process severity and temperature requirements
  Lower process complexity and streamlined distributed scale deployment
  Lower catalyst cost through efficient use of active metals
  Improved catalyst stability by mitigating oxidation of active sites
  Removal of thermodynamic barriers for production of pipeline quality renewable natural gas In an aspect, provided is a catalyst system comprising: a substrate; an atomically dispersed metal catalyst; wherein the catalyst promotes the conversion of biogas into a reaction product.

In an aspect, provided is a method for converting a biogas into $CH_4$ comprising: reacting said biogas in the presence of hydrogen gas and an atomically dispersed transition metal catalyst, thereby generating $CH_4$.

The substrate may be a redox active substrate, for example, $TiO_2$ or $CeO_2$.

The atomically dispersed metal catalyst may be a transition metal, for example, Ni, Ru, Rh, Mo, Pt, or any combination thereof.

The transition metal may be dispersed on the substrate as particles having a characteristic length on the atomic scale.

The step of reacting may be performed at a temperature less than or equal to 400° C., 375° C., 350° C., 325° C., 300° C., or optionally, 250° C. The step of reacting may be performed at a pressure less than or equal to 2 atm, 1.5 atm, or optionally, 1 atm.

The described method may convert the biogas into products comprising predominately $CH_4$. The method may have a conversion rate greater than or equal to 99%, 95%, 90%, or optionally 85%, efficiency to $CH_4$, excluding produced water.

The described catalysts and methods may generate recycled natural gas, recycled natural gas, syngas, liquid fuel precursors, liquid fuel, or any combination thereof, each of which comprises methane.

In an aspect, provided is a system for performing any of the methods described herein.

In an aspect, provided is a catalyst system comprising: a substrate selected from the group of $TiO_2$ or $CeO_2$; an atomically dispersed metal catalyst selected from the group of: Ni, Ru, Rh, Mo, Pt or any combination thereof; wherein the catalyst promotes the conversion of biogas comprising a mixture of $CH_4$ and $CO_2$ into a recycled natural gas comprising greater than 90% $CH_4$, excluding produced water.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF DRAWINGS

Some embodiments are illustrated in referenced figures of the drawings. It is intended that the embodiments and figures disclosed herein are to be considered illustrative rather than limiting.

DETAILED DESCRIPTION

Figure 1:
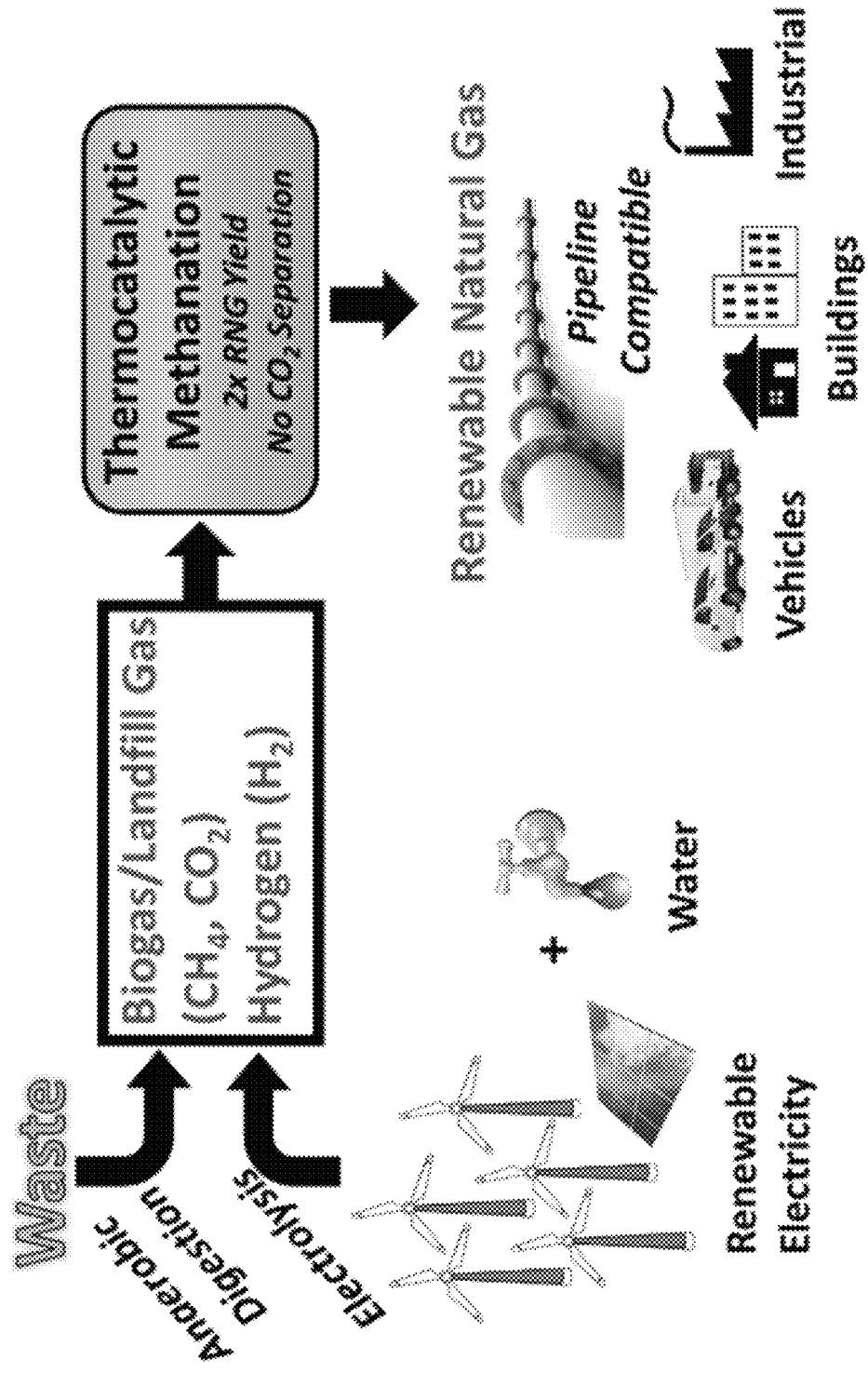
FIG. 1 illustrates a process with integrated methanation/electrolysis to maximize the yield of RNG, eliminate $CO_2$ separation requirements, and link wet waste systems to local sustainable energy infrastructure.

The embodiments described herein should not necessarily be construed as limited to addressing any of the particular problems or deficiencies discussed herein. References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein the term "substantially" is used to indicate that exact values are not necessarily attainable. By way of example, one of ordinary skill in the art will understand that in some chemical reactions 100% conversion of a reactant is possible, yet unlikely. Most of a reactant may be converted to a product and conversion of the reactant may asymptotically approach 100% conversion. So, although from a practical perspective 100% of the reactant is converted, from a technical perspective, a small and sometimes difficult to define amount remains. For this example of a chemical reactant, that amount may be relatively easily defined by the detection limits of the instrument used to test for it. However, in many cases, this amount may not be easily defined, hence the use of the term "substantially". In some embodiments of the present invention, the term "substantially" is defined as approaching a specific numeric value or target to within 20%, 15%, 10%, 5%, or within 1% of the value or target. In further embodiments of the present invention, the term "substantially" is defined as approaching a specific numeric value or target to within 1%, 0.9%, 0.8%, 0.7%, 0.6%, 0.5%, 0.4%, 0.3%, 0.2%, or 0.1% of the value or target.

As used herein, the term "about" is used to indicate that exact values are not necessarily attainable. Therefore, the term "about" is used to indicate this uncertainty limit. In some embodiments of the present invention, the term "about" is used to indicate an uncertainty limit of less than or equal to ±20%, ±15%, ±10%, ±5%, or ±1% of a specific numeric value or target. In some embodiments of the present invention, the term "about" is used to indicate an uncertainty limit of less than or equal to ±1%, ±0.9%, ±0.8%, ±0.7%, ±0.6%, ±0.5%, ±0.4%, ±0.3%, ±0.2%, or ±0.1% of a specific numeric value or target.

As used herein, the term "atomically dispersed" refers to a catalyst with highly dispersed active catalyst metal sites. In some embodiments, for example, the metal sites may be individual atoms (as a single atom catalyst) or small groupings of atoms (e.g., less than or equal to 5 atoms, 10 atoms, 25 atoms or 50 atoms). The metal sites may be dispersed on a substrate, as described herein. The relative mass of the metal sites may be significantly less than that of the substrate on which they are deposited, for example, less than or equal to 1 wt %, 0.5 wt %, 0.25 wt %, 0.1 wt %, or optionally, 0.05 wt %. An atomically dispersed catalyst may be prepared using a method of strong electrostatic adsorption (SEA).

As used herein, the term "biogas" refers to a waste gas stream from industrial or agricultural processes, for example, landfills, wastewater treatment facilities or agricultural digesters. Biogas may comprise a mixture of methane and carbon dioxide. Biogas may include small concentrations of impurities (e.g., sulfur, siloxanes) which will differ based on the biogas source.

As used herein, the term "characteristic length" refers to an average length of a molecule. The characteristic length may be on the atomic scale, meaning that greater than 50%, 75%, 90% or 95% of the molecules are individual atoms or molecules having less that 2 or 5 atoms.

As used herein, the term "atomically dispersed" refers to a plurality of atoms that are separated by a space greater than or equal to the size of an at least one, at least two or at least 5 atoms of the compound being described. Atomically dispersed may refer to a plurality of atoms wherein at least 50%, 75%, 90% or 95% are deposited as individual atoms.

The provided discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

Example 1—Methanation of Biogas for Enhanced Yield

Biogas from landfills, wastewater treatment facilities, and agricultural digesters is an abundant resource for the production of renewable natural gas (RNG), which can be integrated into the existing pipeline infrastructure and used for a variety of applications, including as a fuel for medium- and heavy-duty vehicles. However, conventional biogas-to-RNG technologies require the separation of $CO_2$ using incumbent technologies such as pressure swing adsorption. This approach is cost-intensive, and discarding $CO_2$ limits the overall carbon yield of RNG to <50-60% of its theoretical potential. Methanation of biogas-derived $CO_2$ represents a preferred pathway which can double RNG yield and eliminate the need for $CO_2$ separation.

Methanation of Biogas for Enhanced Yield (MOBEY) is described herein: $CO_2$ separation units are replaced with a methanation reactor system to promote the conversion of $CO_2$ into $CH_4$ (FIG. 1). Utilizing $CO_2$ as a feedstock allows for elimination of $CO_2$ separation step, greater RNG yields, and a simplified biogas cleanup process. Moreover, the renewable hydrogen required for methanation can be supplied via electrolysis operated in a dynamic mode to balance fluctuations in renewable electricity production. In this approach, low-cost renewable electricity is directed towards hydrogen production, which is stored and utilized in the methanation reaction to produce RNG. Producing RNG that is compatible with existing pipeline infrastructure enables the conversion of electrical to chemical energy in a form that is versatile and easily transported, effectively linking wet waste energy systems to local sustainable energy infrastructure.

Conventional methanation catalysts (e.g., Ni/Al$_2$O$_3$) are highly susceptible to impurities in the biogas stream, (e.g., sulfur, siloxanes), which can lead to rapid and irreversible deactivation. Additionally, these materials are most active at >400° C. However, operating at these temperatures induces thermodynamic constraints on CO$_2$ conversion that limit methane purity to below pipeline requirements. Consequently, the development of highly productive catalysts which are effective for co-processing CO$_2$ and CH$_4$, active at temperatures ≤350° C., and compatible with biogas impurities represents an improvement to biogas-to-RNG processes.

Figure 2:
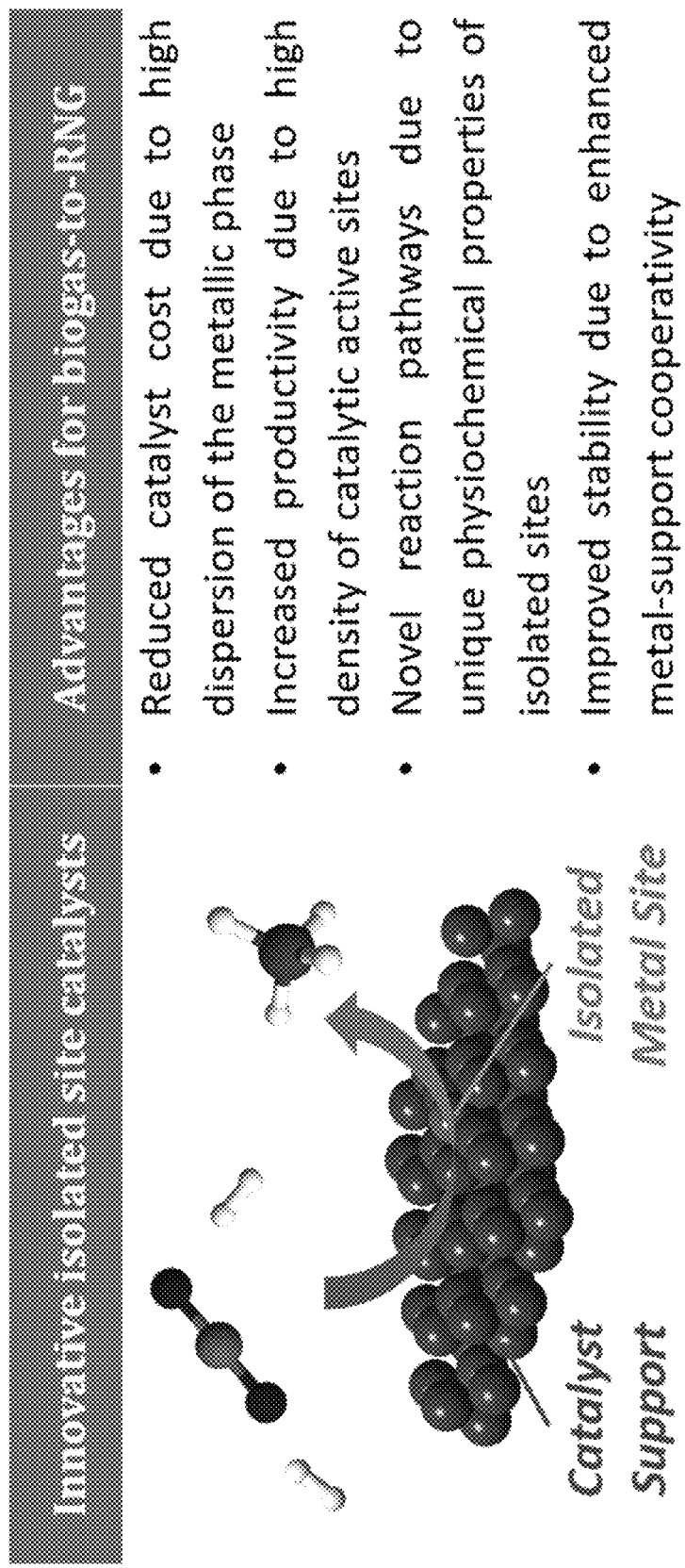
FIG. 2 illustrates the improved performance over catalyst containing atomically dispersed metal sites.

The described process directly addresses these barriers through innovative catalyst development to boost productivity, enable the co-processing of CO$_2$ and CH$_4$, and reduce poisoning by biogas impurities. An important aspect involves the synthesis of novel monometallic and bimetallic catalytic materials containing atomically dispersed metal sites (FIG. 2). The ultra-high dispersion of these catalysts maximizes the efficiency of metal usage, and single site active centers exhibit unique physiochemical properties compared to nanoparticles. In previous reports, these advantages have translated to improved activity for low-temperature methane oxidation and greater stability during methane dehydroaromatization, but this class of catalyst has not been investigated for biogas methanation. The improved performance of these catalysts will advance the state of the art by increasing productivity, improving stability, and lowering capital costs due to reduced reactor volumes and temperature requirements. Coupled with technology advancement in electrolysis and an improved economic outlook in which electrical grid managers are likely to reward flexibility, the outcomes of this project have a strong likelihood of enabling a positive business case for biogas-to-RNG. Current results demonstrate a 10× improvement in methane production rates on a metal mass basis compared to a conventional Ni/Al$_2$O$_3$ methanation catalyst.

Described herein is a process to advance biogas-to-RNG technologies by improving catalytic productivity and removing CO$_2$ separation requirements. This is achieved through catalysis and processes developed to promote low temperature conversion of CO$_2$ into CH$_4$ with quantitative yields (Eq. 1).

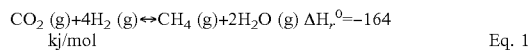

$$CO_2\ (g) + 4H_2\ (g) \leftrightarrow CH_4\ (g) + 2H_2O\ (g)\ \Delta H_r^0 = -164\ kj/mol \quad \text{Eq. 1}$$

By co-processing CO$_2$, we eliminate the need for incumbent separation technologies such as pressure swing adsorption. Moreover, utilizing renewable hydrogen supplied via electrolysis provides an opportunity to link existing electrical and gas infrastructure in order to balance fluctuations in renewable electricity production.

Figure 3:
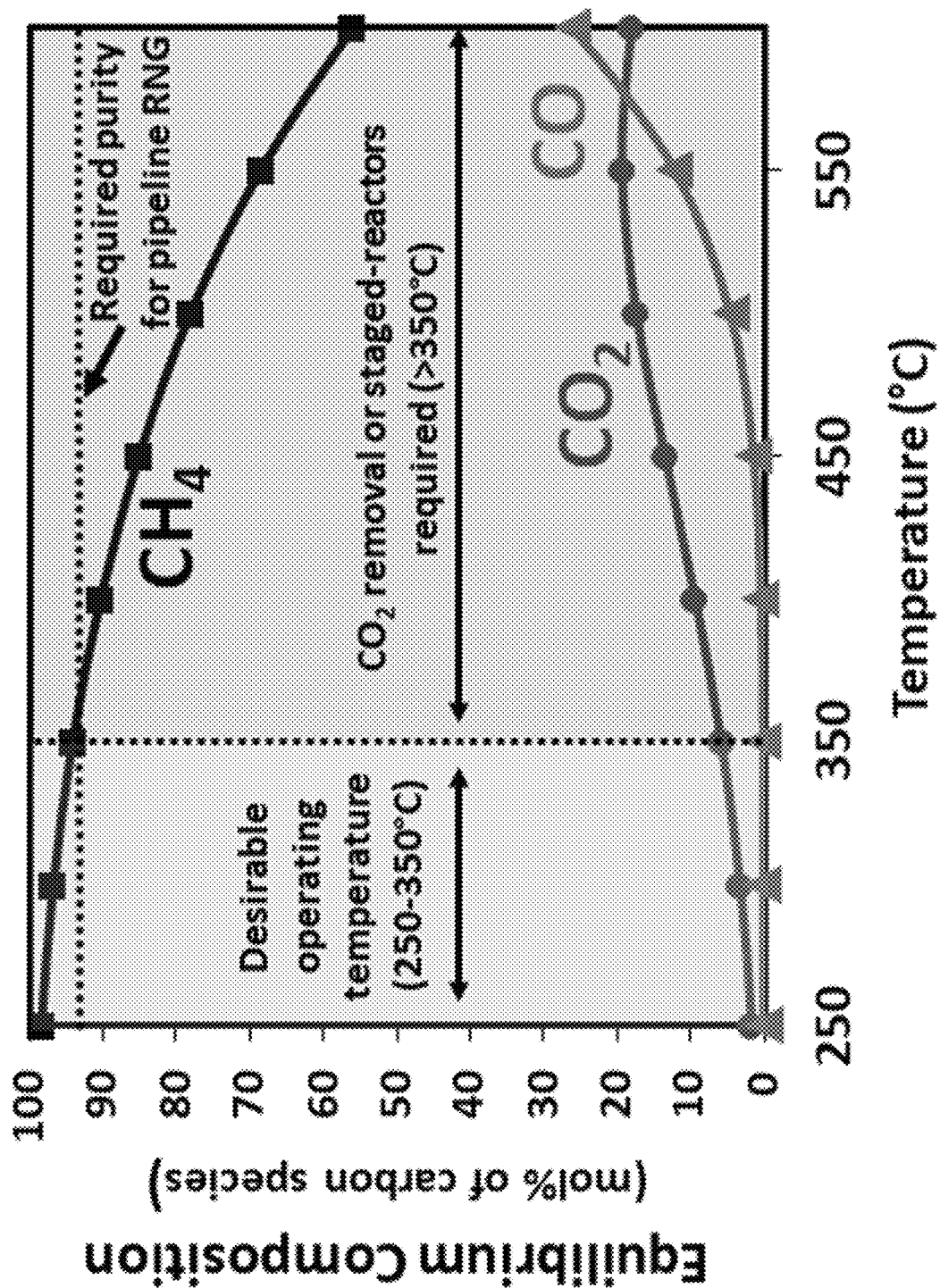
FIG. 3 illustrates the thermodynamic equilibrium for biogas during methanation showing the opportunity for catalysts operating at ≤350° C. to create pipeline quality RNG. Initial composition: 1:1:4 $CO_2/CH_4/H_2$, 1 atm.

Thermochemical methanation (i.e., the Sabatier reaction) has been practiced since 1902, and due to the high productivity and potential for commercialization, catalyst development for CO$_2$ methanation has attracted a considerable amount of attention. However, minimal research has focused on applying methanation catalysts for co-processing of biogas-derived CO$_2$ and CH$_4$. Consequently, open questions remain regarding the potential impacts of CH$_4$ as a co-reactant and the presence of impurities of the biogas stream. For example, Ni/Al$_2$O$_3$ catalysts are commonly utilized for CO$_2$ methanation due to their low cost and high selectivity to CH$_4$. However, several drawbacks limit the application of this material for the distributed-scale conversion of biogas to RNG:

Ni/Al2O3 exhibits the highest productivity at >400° C. However, operating at these temperatures induces thermodynamic constraints on CO2 conversion that limit methane purity to below pipeline requirements (FIG. 3)

Conventional Ni catalysts with high metal loading and large particle size form CO as a byproduct, necessitating additional separation steps.

Ni/Al2O3 catalysts are highly susceptible to impurities in the biogas feedstock (e.g., sulfur, siloxanes), which can lead to rapid and irreversible deactivation.

Thus, highly productive catalysts which are active at temperatures ≤350° C. and compatible with biogas impurities represents an important innovation to enable biogas-to-RNG. The described intensified process overcomes these challenges through integrative catalyst and process development with a focus on monometallic and bimetallic catalytic materials containing atomically dispersed metal sites (e.g., Ni, Ru, Rh, Mo). The ultra-high dispersion of these catalysts maximizes the efficiency of metal usage, which in turn enables a reduction in metal loading and a corresponding improvement in catalyst cost. Additionally, this approach enables a wider variety of potential catalysts that meet specific cost targets, opening opportunities for unique formulations and chemistries that have previously been cost-prohibitive. For example, estimates from the EERE-developed ChemCatBio CatCost tool suggest that the price for an atomically dispersed 0.1 wt % Mo catalyst is roughly half that of a conventional 6 wt % Ni catalyst. Moreover, single site active centers exhibit unique physiochemical properties compared to nanoparticles, and their relative homogeneity provides for precise interactions with reactants, leading to more control over selectivity and product distribution. In previous reports, these advantages have translated to improved activity for low-temperature methane oxidation and greater stability during methane dehydroaromatization, but this innovative approach has not been investigated for biogas methanation. Maximizing catalyst dispersion also allows us to leverage support cooperativity to improve performance. Preliminary data from our laboratory suggests that utilizing redox active support materials (e.g., TiO$_2$, CeO$_2$) can increase RNG yields due to the presence of amphoteric CO$_2$ binding sites at the metal-support interface, and this class of support will improve sulfur tolerance by modifying the electronic structure of the metallic phase, as has been demonstrated during other hydrogenation reactions.

The conversion of CO$_2$ to produce CH$_4$ is a thermodynamically favored at low temperatures, and when T>350° C. the equilibrium composition from biogas (1:1:4 CO$_2$, CH$_4$, H$_2$) is such that a single reactor cannot produce pipeline quality renewable natural gas without additional CO$_2$ separation (FIG. 3). As such, described are catalysts capable of operating at low temperatures (≤350° C.) to enable a single-stage reactor to produce pipeline quality RNG. Using commercially scalable synthetic techniques we have developed a series of catalysts with the capability of activating H$_2$ and CO$_2$ at lower temperatures than the benchmark Ni/Al$_2$O$_3$ methanation catalyst.

Figure 4:
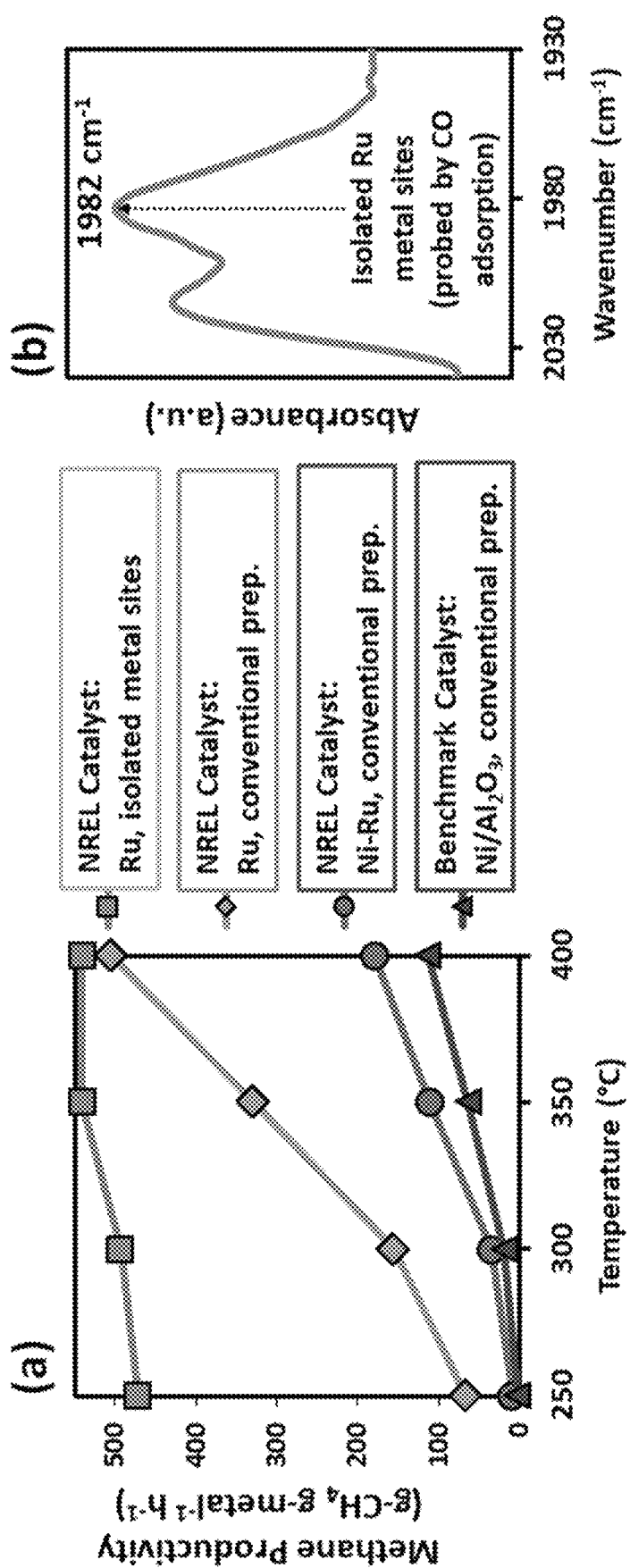
FIG. 4 provides data showing (a) higher activity for biogas methanation over novel catalysts as compared to the benchmark catalyst. Reaction conditions: 1:1:4 $CO_2/CH_4/H_2$, 1 atm, 200 sccm, 100 mg catalyst. (b) Presence of highly dispersed, isolated Ru sites using CO adsorption and infrared spectroscopy.
Figure 5:
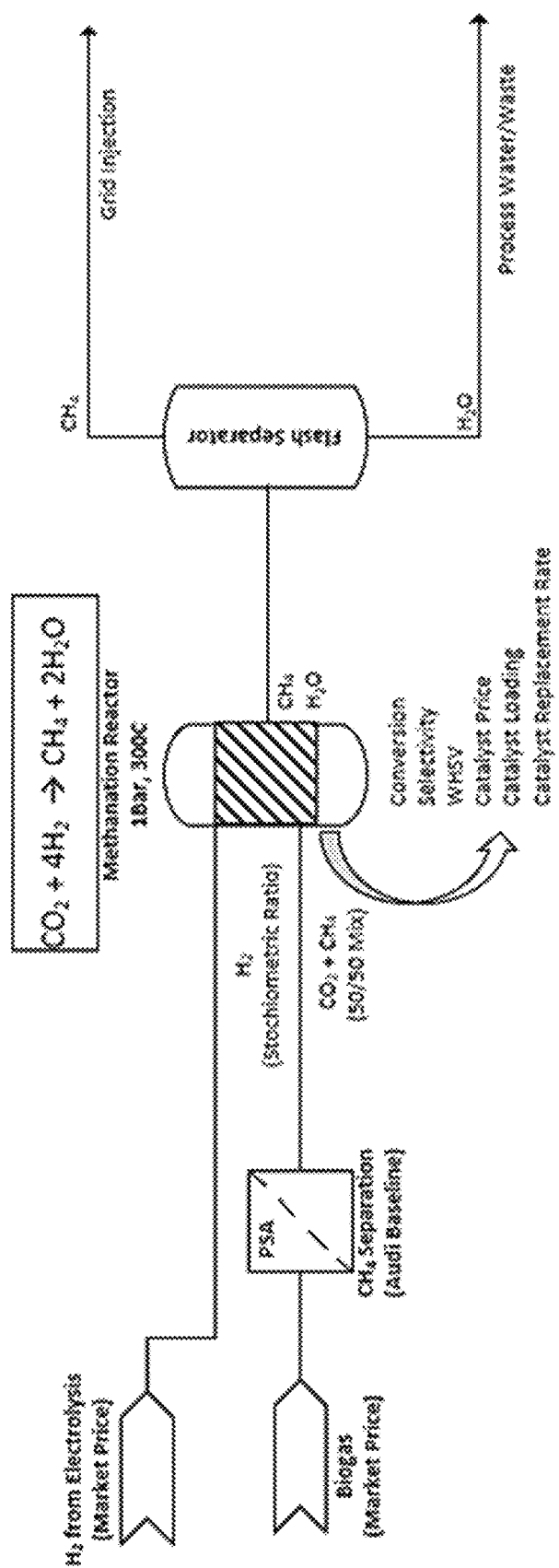
FIG. 5 provides a simplified process flow diagram.

Proof-of-concept experiments with synthetic biogas have demonstrated a 10× improvement in the low temperature rate of CO$_2$ conversion based on a metal loading basis over a catalyst containing atomically dispersed Ru sites as compared to a benchmark, Ni/Al$_2$O$_3$ baseline (FIG. 4a). As such, these materials require less active metal/catalyst loading to reach equilibrium yields of methane at T≤350° C., enabling a single-step conversion to produce pipeline quality renewable natural gas. The presence of isolate Ru sites on the described catalysts is confirmed by spectroscopic data provided in FIG. 4b, which shows a characteristic peak at 1984 cm$^{-1}$ that is attributed to $CO_{ad}$ species adsorbed on-top of highly dispersed, low coordinated Ru clusters isolated from other metal particles.

The described process shares some commonalities with emerging biological methanation pathways. However, the described thermochemical approach is advantaged due to the lack of mass transfer limitations that hinder biological pathways. These barriers occur between the gas and liquid phase and contribute to lower than desired productivities, resulting in biological methane production rates on the order of 1-2 g/L*h. Our thermochemical approach exhibits much higher productivities by avoiding mass transfer limitations and processing methane in the vapor phase. For example, experiments have demonstrated methane productivity values of 12.6 g/g-cat/h (with catalyst density of 550 g/L), representing a 3-4× order of magnitude improvement over the biological state of technology. These thermochemical productivity values are un-optimized, and significant increases are expected through the catalyst and process development.

The described invention may be further understood by the following non-limiting examples:

1. A catalyst system comprising:
   a substrate comprising a metal oxide;
   an atomically dispersed transition metal;
   wherein said catalyst promotes the conversion of $CO_2$ and $H_2$ into $CH_4$.
2. The catalyst system of example 1, wherein said substrate is a redox active substrate.
3. The catalyst system of example 2, wherein said substrate comprises $TiO_2$ or $CeO_2$.
4. The catalyst system of any of examples 1-3, wherein said transition metal is dispersed on the substrate as particles having a characteristic length on the atomic scale.
5. The catalyst system of example 4, wherein said metal catalyst is selected from the group of Ni, Ru, Rh, Mo, Pt, or any combination thereof.
6. A method for converting a biogas into $CH_4$ comprising: reacting said biogas in the presence of hydrogen gas and an atomically dispersed transition metal catalyst, thereby generating $CH_4$.
7. The method of example 6, wherein said biogas comprises $CO_2$, $CH_4$, or a combination thereof.
8. The method of example 6 or 7, wherein said atomically dispersed metal catalyst is provided on a substrate.
9. The method of example 8, wherein said substrate is a redox active substrate.
10. The method of example 8 or 9, wherein said transition metal is dispersed on the substrate as particles having a characteristic length on the atomic scale.
11. The method of any of examples 8-10, wherein said substrate comprises $TiO_2$ or $CeO_2$.
12. The method of any of examples 6-11, wherein said metal catalyst is a transition metal.
13. The method of any of examples 6-12, wherein said metal catalyst is selected from the group of Ni, Ru, Rh, Mo, Pt, or any combination thereof
14. The method of any of example s 6-13, wherein said step of reacting is performed at a temperature less than or equal to 350° C.
15. The method of any of example s 6-14, wherein said step of reacting is performed at a pressure less than or equal to 1 atm.
16. The method of any of examples 6-15, wherein said method converts said biogas into $CH_4$.
17. The method of example 16, wherein said method has a conversion rate greater than or equal to 90% efficiency to $CH_4$, excluding produced water.
18. A catalyst system comprising:
   a substrate selected from the group of $TiO_2$ or $CeO_2$;
   an atomically dispersed metal selected from the group of: Ni, Ru, Rh, Mo, Pt or any combination thereof;
   wherein said catalyst promotes the conversion of biogas comprising a mixture of $CH_4$ and $CO_2$ into a recycled natural gas comprising greater than 90% $CH_4$, excluding produced water.
19. The system of example 18, wherein said atomically dispersed metal is dispersed on the substrate as particles having a characteristic length on the atomic scale.
20. The system of examples 18 or 19, wherein said catalyst system is capable of generating the recycled natural gas at a temperature less than or equal to 350° C. and at a pressure less than or equal to 1 atm.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods, and devices useful for the present methods can include a large number of optional composition and processing elements and steps.

As used herein and in the appended claims, the singular forms "a", "an", and "the" include plural reference unless the context clearly dictates otherwise. Thus, for example, reference to "a cell" includes a plurality of such cells and equivalents thereof known to those skilled in the art. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure. For example, when a device is set forth disclosing a range of materials, device components, and/or device configurations, the description is intended to include specific reference of each combination and/or variation corresponding to the disclosed range.

Every formulation or combination of components described or exemplified herein can be used to practice the invention, unless otherwise stated.

Whenever a range is given in the specification, for example, a density range, a number range, a temperature range, a time range, or a composition or concentration range, all intermediate ranges, and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A catalyst system comprising:
a substrate comprising a metal oxide;
an atomically dispersed transition metal comprising Mo;
wherein the atomically dispersed transition metal is dispersed in groupings less than or equal to 50 atoms;
wherein said catalyst promotes the conversion of $CO_2$ and $H_2$ into $CH_4$.

2. The catalyst system of claim 1, wherein said substrate is a redox active substrate.

3. The catalyst system of claim 2, wherein said substrate comprises $TiO_2$ or $CeO_2$.

4. The catalyst system of claim 1, wherein the atomically dispersed transition metal is provided in an amount less than or equal to 1 wt % based on a total wt % of the catalyst.

5. A catalyst system comprising:
a substrate selected from the group consisting of $TiO_2$ and Of $CeO_2$;
an atomically dispersed transition metal comprising Mo;
wherein the atomically dispersed transition metal is dispersed in groupings less than or equal to 50 atoms;
wherein said catalyst promotes the conversion of biogas comprising a mixture of $CH_4$ and $CO_2$ into a recycled natural gas comprising greater than 90% $CH_4$, excluding produced water.

6. The catalyst system of claim 5, wherein said catalyst system is capable of generating the recycled natural gas at a temperature less than or equal to 350° C. and at a pressure less than or equal to 1 atm.

7. The catalyst system of claim 5, wherein the atomically dispersed transition metal is provided in an amount less than or equal to 1 wt % based on a total wt % of the catalyst.

* * * * *